(12) United States Patent
Kase

(10) Patent No.: US 7,902,420 B2
(45) Date of Patent: Mar. 8, 2011

(54) BODY ADHESIVE TAPE

(75) Inventor: Kenzo Kase, Tokyo (JP)

(73) Assignee: Kinesio IP, LLC, Albuquerque, NM (US)

( * ) Notice: Subject to any disclaimer, the term of this patent is extended or adjusted under 35 U.S.C. 154(b) by 462 days.

(21) Appl. No.: 10/588,854

(22) PCT Filed: May 20, 2005

(86) PCT No.: PCT/JP2005/009272
§ 371 (c)(1),
(2), (4) Date: Aug. 9, 2006

(87) PCT Pub. No.: WO2006/067876
PCT Pub. Date: Jun. 29, 2006

(65) Prior Publication Data
US 2008/0154169 A1  Jun. 26, 2008

(30) Foreign Application Priority Data
Dec. 24, 2004  (JP) ................. 2004-372719

(51) Int. Cl.
*A61F 13/00* (2006.01)
*A61F 15/00* (2006.01)
*B32B 7/12* (2006.01)
*A61B 17/06* (2006.01)

(52) U.S. Cl. ............... 602/55; 602/41; 602/42; 602/54; 602/903; 428/167; 428/212; 428/343; 206/440

(58) Field of Classification Search ........... 602/52, 602/54, 55, 58, 65, 900, 903, 59; 606/204.35, 606/204.45, 204.15, 204.25; 427/208.4, 208.6, 2.31; 424/402
See application file for complete search history.

(56) References Cited

U.S. PATENT DOCUMENTS

| | | | |
|---|---|---|---|
| 2,310,082 A | | 2/1943 | Holbrooke |
| 3,199,548 A | | 8/1965 | Conant |
| 4,742,826 A | * | 5/1988 | McLorg .................. 606/215 |
| 5,397,298 A | | 3/1995 | Mazza et al. |
| 5,650,214 A | * | 7/1997 | Anderson et al. ........... 428/152 |
| 5,704,905 A | * | 1/1998 | Jensen et al. ............... 602/58 |
| 5,861,348 A | * | 1/1999 | Kase ........................ 442/184 |
| 6,103,369 A | * | 8/2000 | Lucast et al. ............ 428/354 |
| 6,495,229 B1 | * | 12/2002 | Carte et al. .............. 428/40.1 |
| 6,726,386 B1 | * | 4/2004 | Gruenbacher et al. ........ 401/7 |
| 7,220,889 B2 | * | 5/2007 | Sigurjonsson et al. ....... 602/58 |
| 2007/0218269 A1 | * | 9/2007 | Kato et al. ............... 428/304.4 |

FOREIGN PATENT DOCUMENTS

| | | |
|---|---|---|
| JP | U11992110723 | 9/1992 |
| JP | 10-033741 | 2/1998 |
| JP | 2001-245920 | 9/2001 |
| JP | 2002-233545 | 8/2002 |
| JP | 2002-238944 | 8/2002 |

OTHER PUBLICATIONS

International Search Report for PCT/JP2005/009272 dated Jul. 5, 2005.

* cited by examiner

*Primary Examiner* — Patricia M Bianco
*Assistant Examiner* — Victoria Hicks
(74) *Attorney, Agent, or Firm* — Samantha A. Updegraff; Deborah A. Peacock; Peacock Myers, P.C.

(57) ABSTRACT

A body adhesive tape comprising a stretch base material and an adhesive layer with grooves.

31 Claims, 11 Drawing Sheets

[Fig. 1]
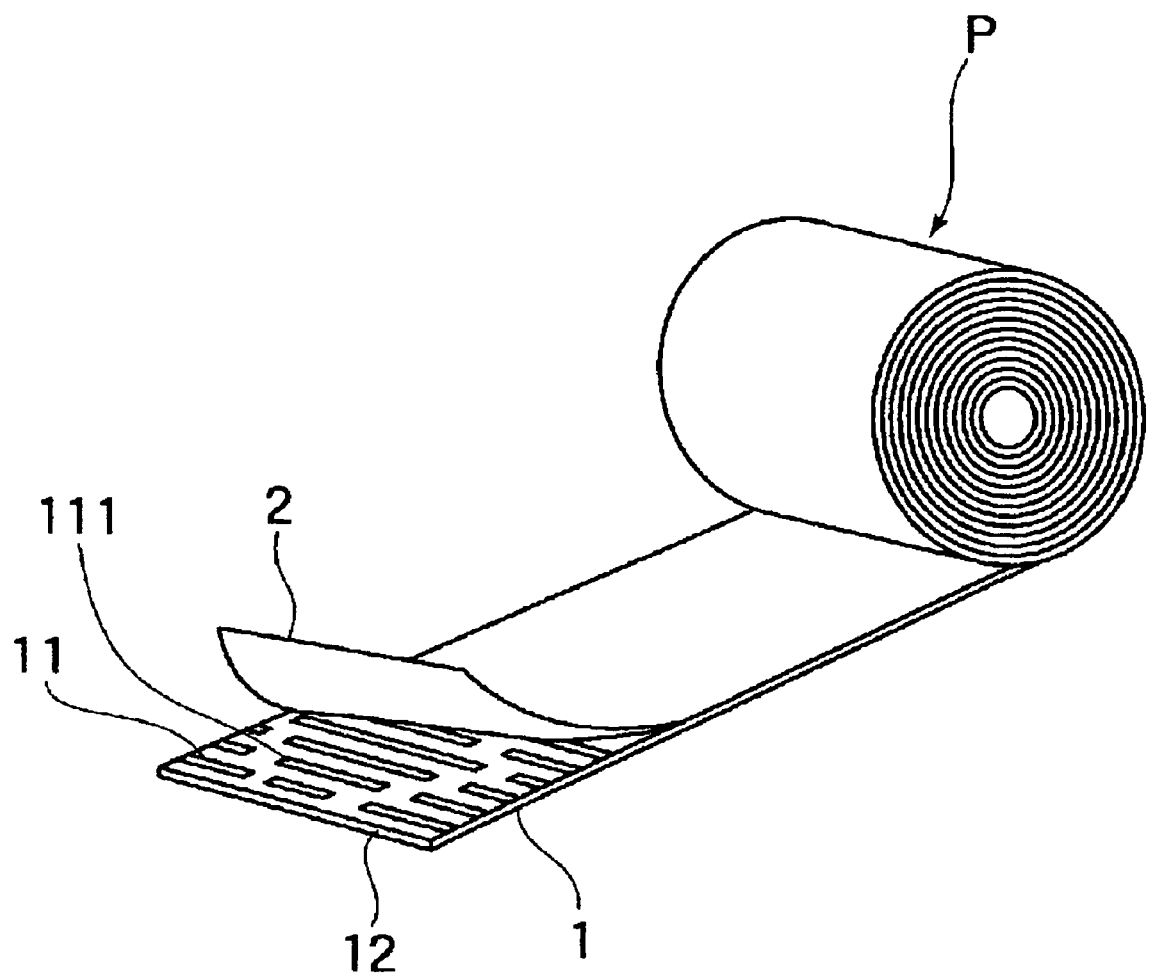

[Fig. 2]
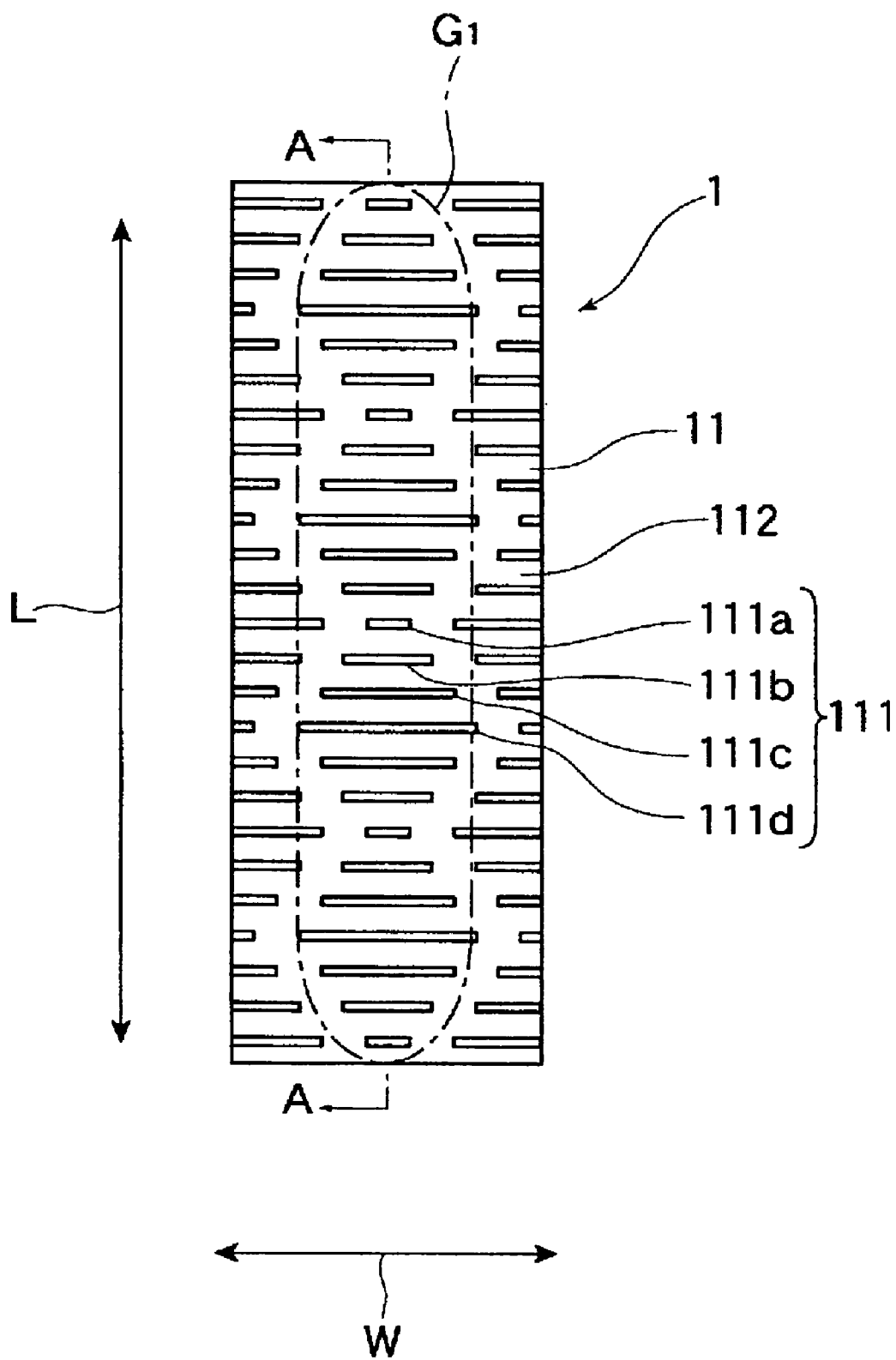

[Fig. 3]
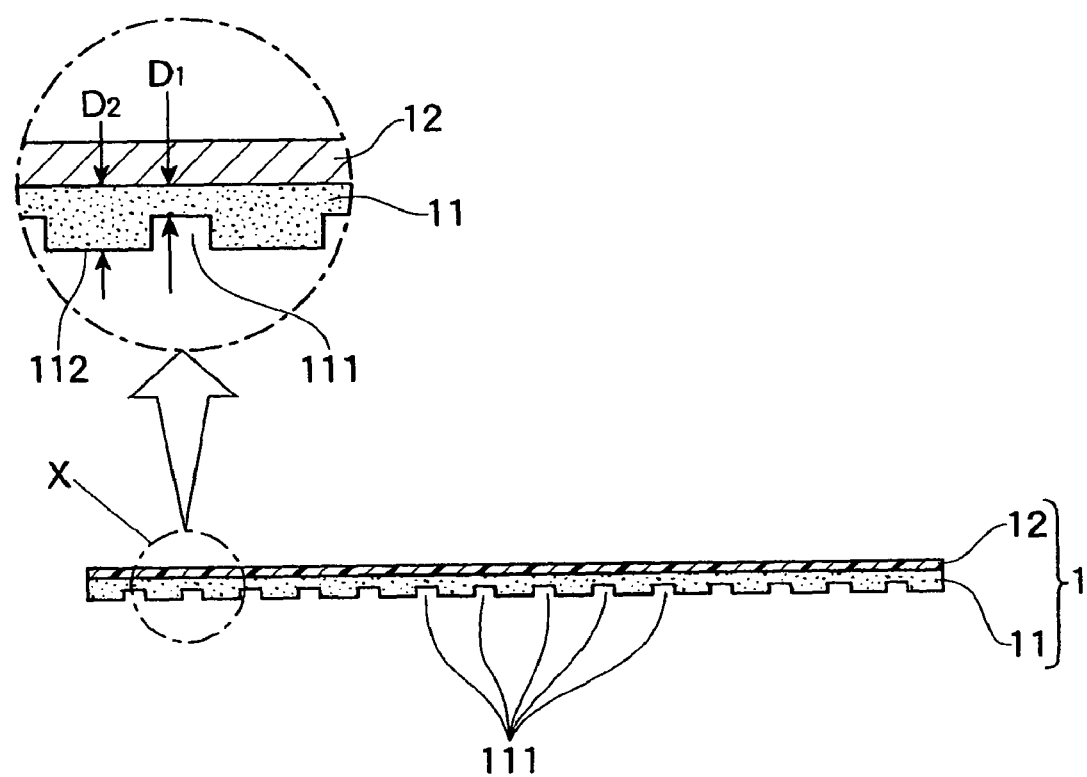

[Fig. 4]
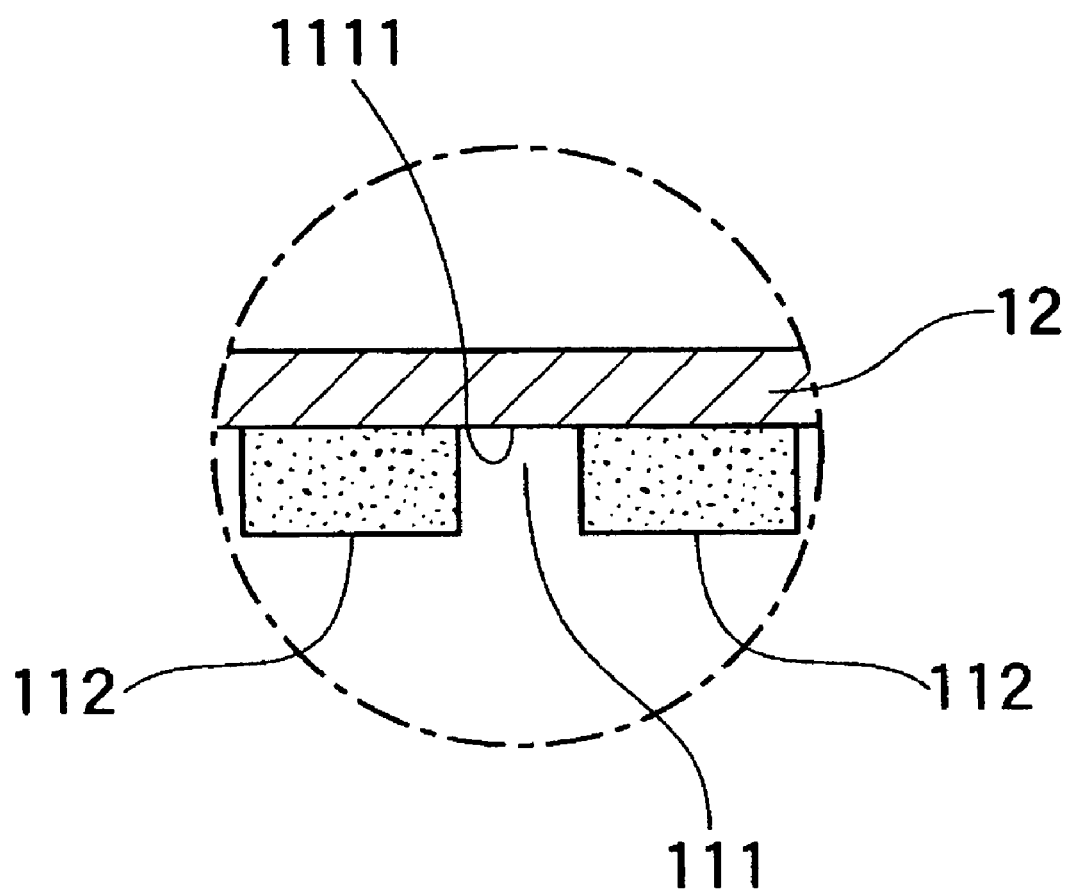

[Fig. 5]
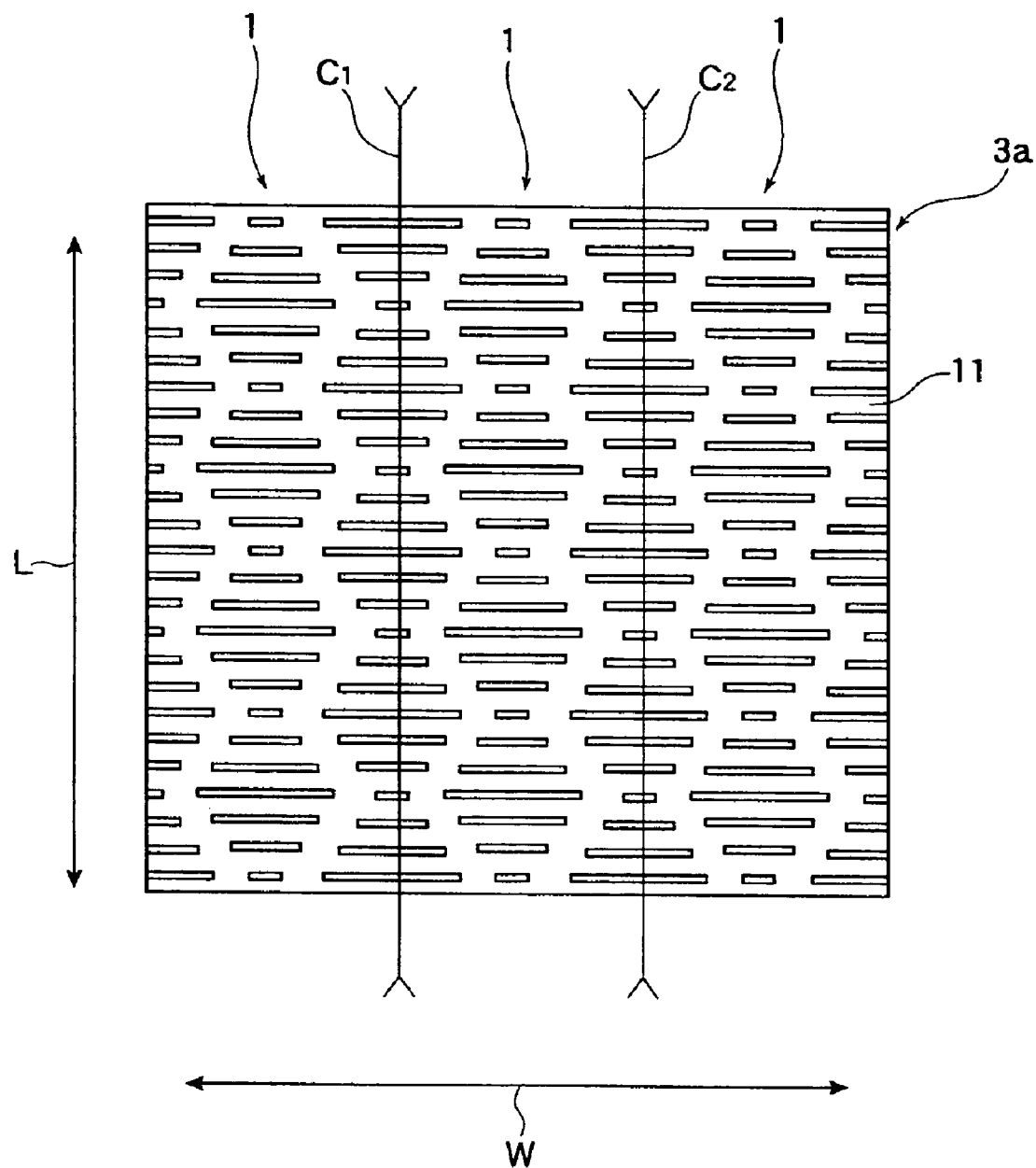

[Fig. 6]
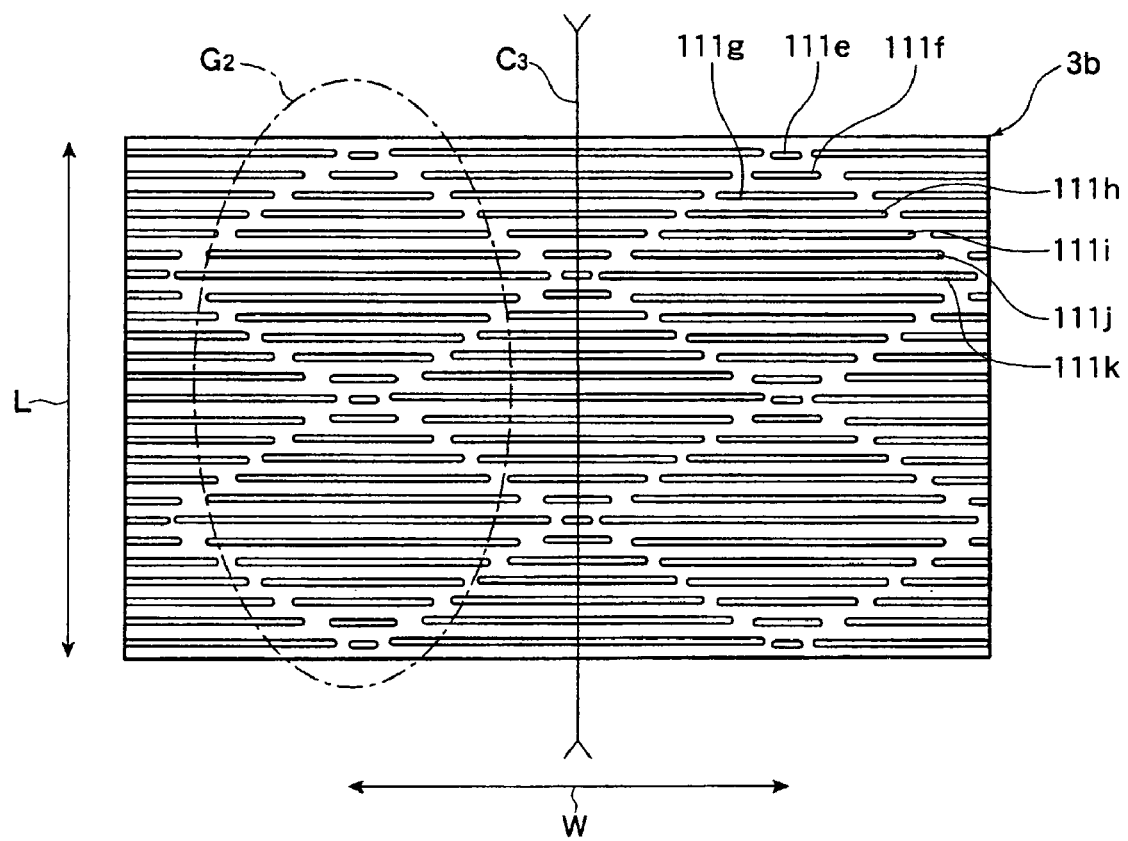

[Fig. 7]
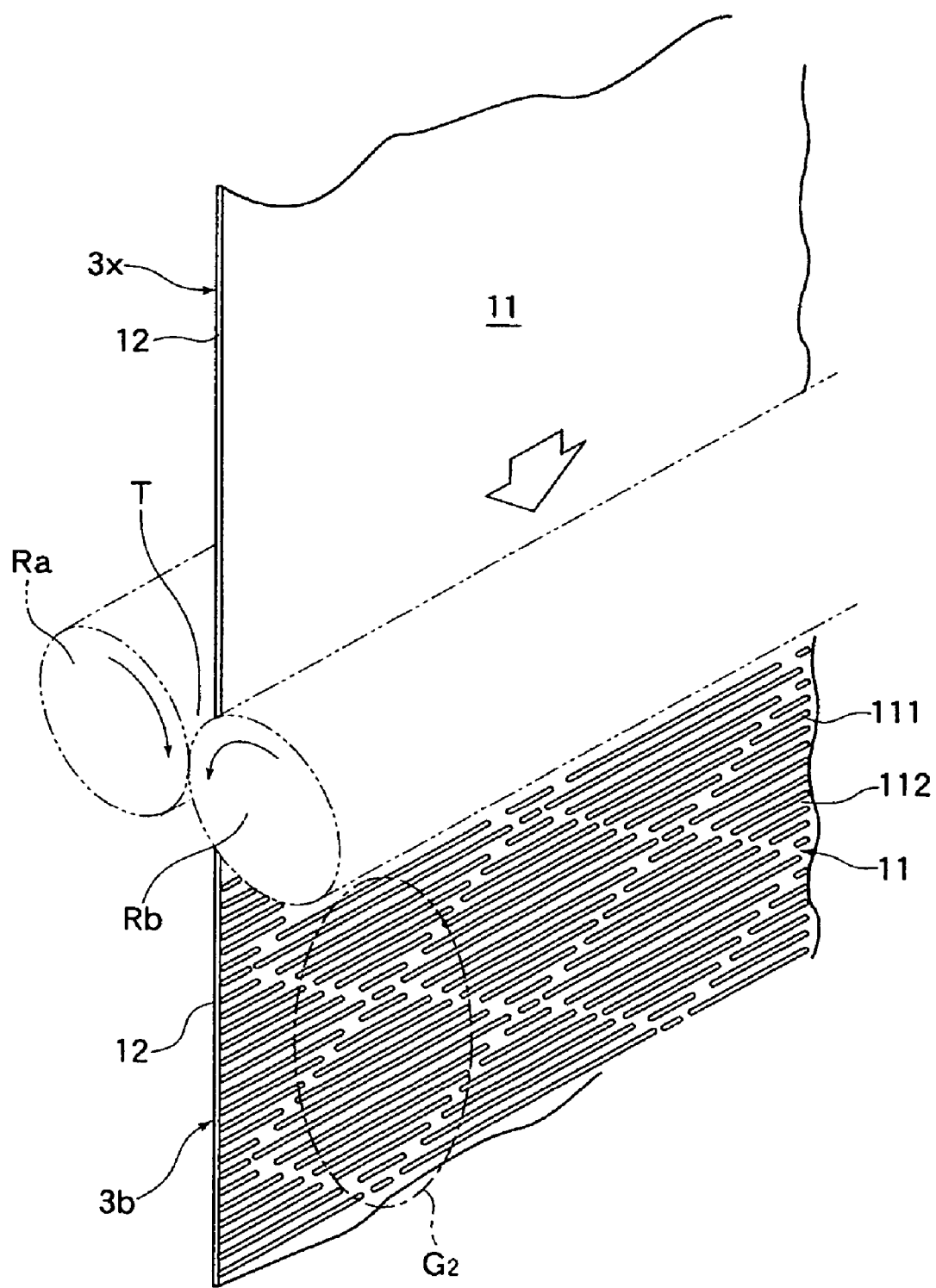

[Fig. 8]
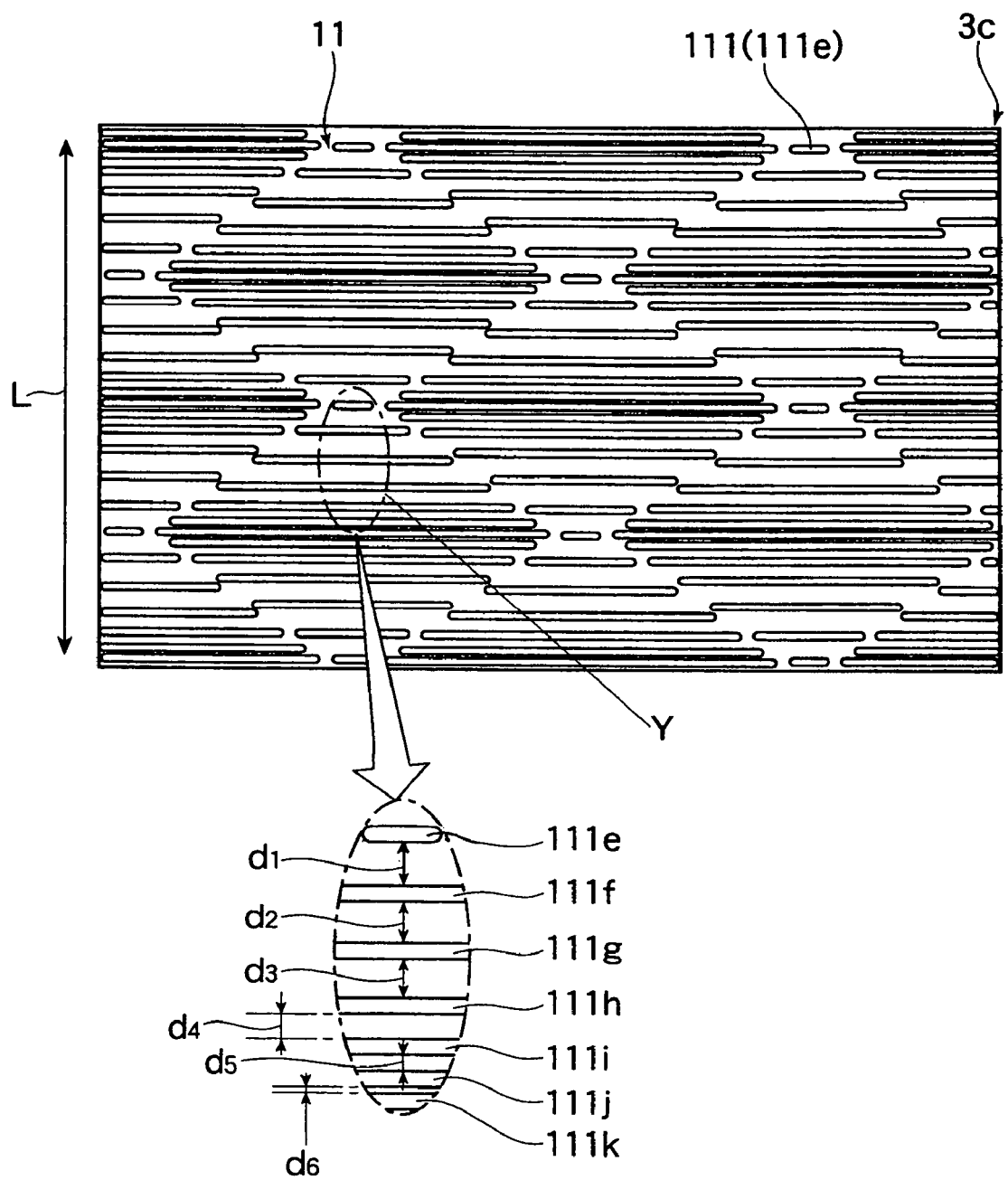

[Fig. 9]
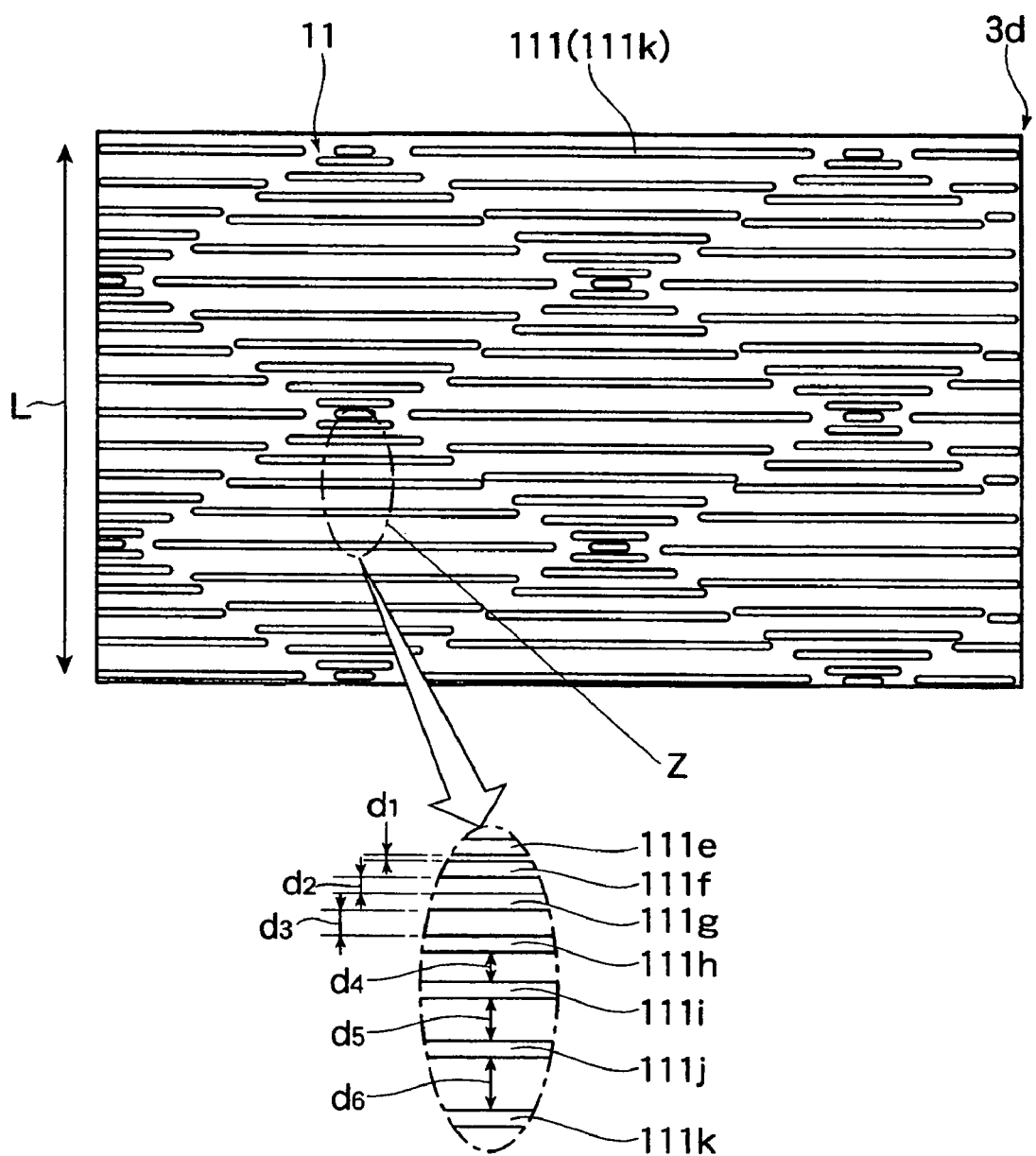

[Fig. 10]
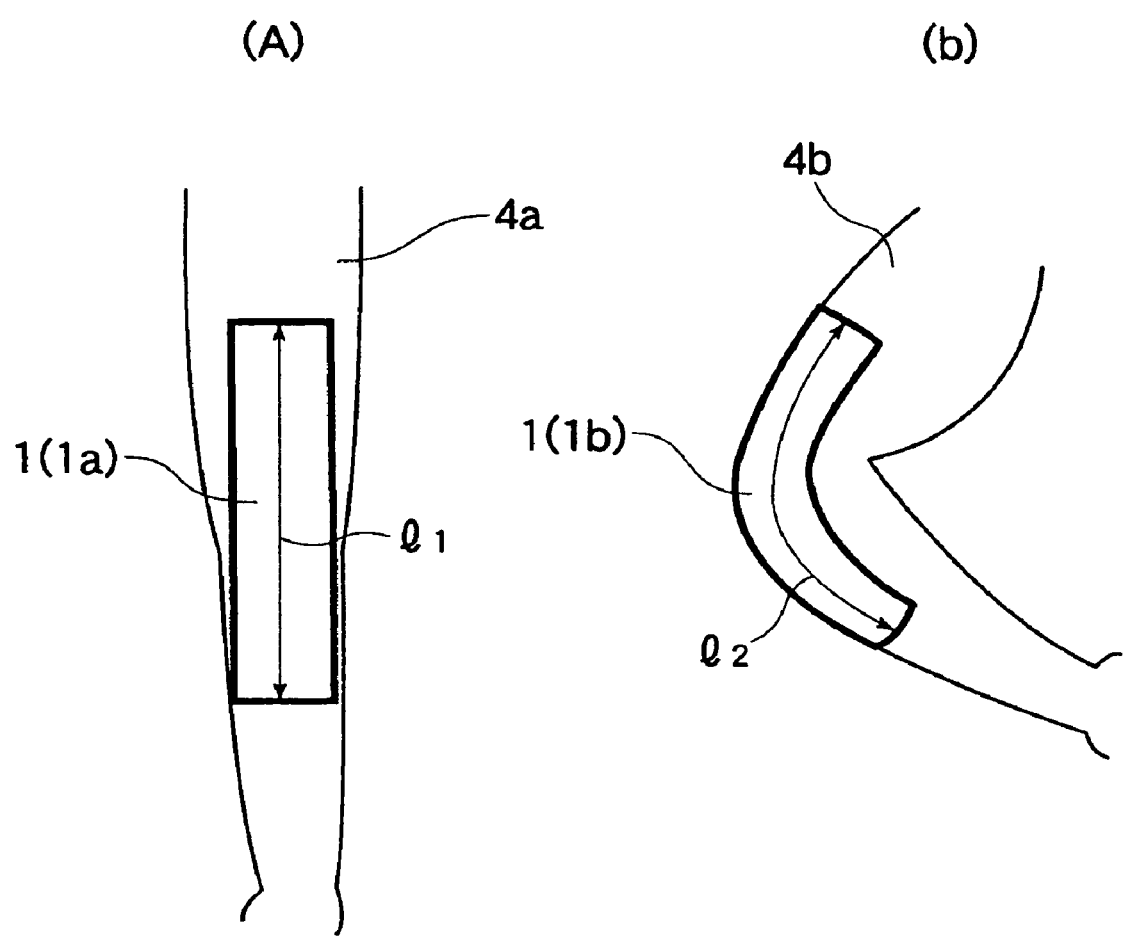

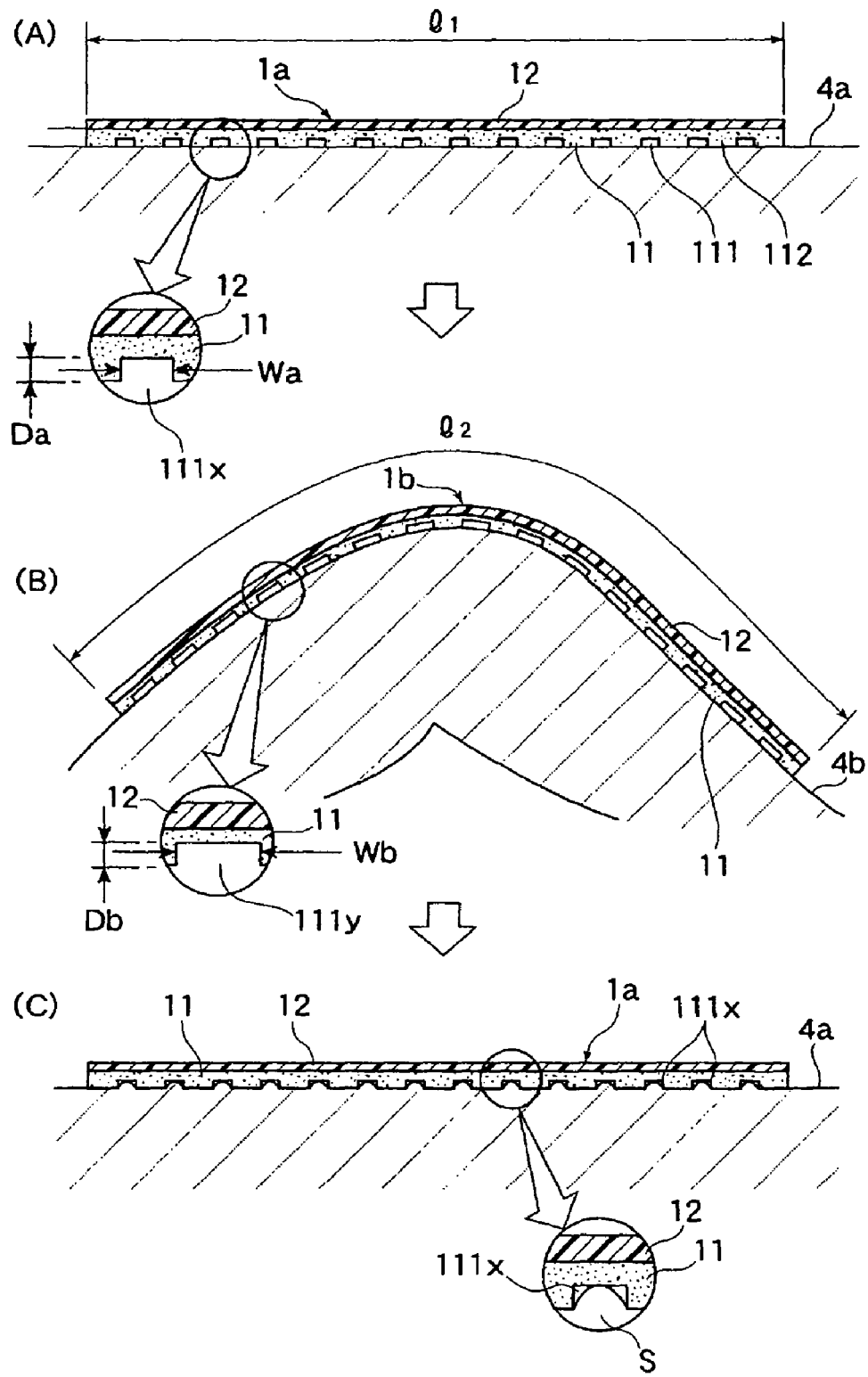
[Fig. 11]

BODY ADHESIVE TAPE

TECHNICAL FIELD

The present invention relates to a tape to be adhered to a body.

BACKGROUND ART

Tape is currently utilized in various fields such as folk remedies, meridian straightening, reflexology, slimming, functional restoration of fascia and muscles, functional restoration of bones and joints, positional correction of tendons, body massage, body insulation, body protection, relief of stiffness such as shoulder stiffness, pain, and inflammation, etc., taping applications, beautification, and treatment of affected body parts.

Such body adhesive tape has been improved in terms of materials, configurations, and/or functions, etc., so as to be able to exhibit the above-exemplified desired effects. For example, there has been proposed some body adhesive tape in which the shape and/or configuration of an adhesive layer is devised.

Patent Document 1 discloses a tape capable of providing stimulus to skin with no strain when stuck to an affected part. This tape is characterized in that a plurality of slit portions extending in the tape longitudinal direction is formed in the tape width direction.

Patent Document 2 discloses a tape having a similar function as that in Patent Document 1, in which slit portions having a predetermined length and extending in the tape longitudinal direction are formed intermittently in the width direction.

Patent Document 3 discloses a breathable tape less likely to be peeled off during sweating. With this tape, a sinuous linear clearance through which creases of a base material are exposed is formed in an adhesive layer.

Patent Document 4 discloses a tape effective against shoulder stiffness, headaches, cramps, joint pain, and muscle pain. This tape is characterized by including two adhesive layers, the first and second adhesive layers being apart from each other at a predetermined distance.

Patent Document 1: Japanese Patent Laid-Open Publication No. 2002-238944
Patent Document 2: Japanese Patent Laid-Open Publication No. 2002-233545
Patent Document 3: Japanese Patent Laid-Open Publication No. Hei 10-033741
Patent Document 4: Japanese Patent Laid-Open Publication No. 2001-245920

DISCLOSURE OF THE INVENTION

Problems to be Solved by the Invention

It is a main object of the present invention to provide a body adhesive tape in which the shape of an adhesive layer is devised to improve the breathability thereof, the tape being adapted to be applied to a body in such a manner as to lift the skin to make it possible to provide stimulus to the body.

Means for Solving the Problems

First, the present invention provides a body adhesive tape including at least a stretch base material and an adhesive layer on one surface of the base material, wherein in the adhesive layer, a plurality of recessed grooves extending in the tape width direction are arranged at a spacing in the tape longitudinal direction and there is provided an array configuration composed of pattern arrays in which the length of the recessed grooves changes stepwise repeating a gradual increase and decrease in the tape longitudinal direction.

The width of the recessed grooves extending in the tape width direction changes with expansion and contraction of the tape in the longitudinal direction, and the thickness of the adhesive layer also changes, which therefore results in a change in the depth of the recessed grooves. For example, the width Wb of the recessed grooves in a state where the tape is expanded is greater than the width Wa of the recessed grooves in a state where the tape is not expanded (Wb>Wa), while the depth Db of the recessed grooves in a state where the tape is expanded is smaller than the depth Da of the recessed grooves in a steady state where the tape is not expanded (Db<Da).

The present invention positively utilizes changes in the width and depth of the recessed grooves associated with expansion and contraction of the tape. Specifically, when the tape is applied to a target part (e.g. neck, elbow, knee, wrist, or lumbar) of a body in a steady state (with no expansion), the convex surface portions of the adhesive layer are attached to the skin. When the body part is bent (e.g. the elbow or knee is bent), the tape becomes expanded and therefore the width of the recessed grooves is increased, while the depth thereof is reduced. Then, when the body is brought back into the original state again, each recessed groove has a function of holding and lifting the skin during the process of reduction in width. This function provides stimulus to fascial and/or muscular tissue under the skin and also increases blood flow and/or lymphatic flow.

The body adhesive tape may be obtained by cutting a sheet on which the pattern arrays of the recessed grooves are disposed parallel with each other at a predetermined spacing in the tape width direction into a desired width. In this case, the body adhesive tape forms an array pattern of a group of recessed grooves in which the pattern arrays are adjacent wholly or partially to each other in accordance with the length of the recessed grooves and/or the width of the tape (cut positions).

In the pattern arrays of a group of recessed grooves, the recessed grooves may be arranged to have the same spacing therebetween. Alternatively, the tape may be devised, in accordance with the intended use and/or application thereof, in such a manner that the spacing between adjacent recessed grooves decreases stepwise from the shortest recessed groove toward the longest recessed groove, or vice versa, that the spacing between adjacent recessed grooves increases stepwise from the shortest recessed groove toward the longest recessed groove.

Effects of the Invention

The body adhesive tape according to the present invention positively utilizes changes in the width and depth of the recessed grooves in the adhesive layer associated with expansion and contraction of the tape in the case of, for example, body bending motions so that the recessed grooves lift the skin in a grasping or holding manner, whereby it is possible to provide stimulus to fascial and/or muscular tissue under the skin and also increase blood flow and/or lymphatic flow, and further to activate natural expanding and contracting motions of muscular tissue.

BEST MODE FOR CARRYING OUT THE INVENTION

A preferred embodiment of the present invention will be described with reference to the accompanying drawings. It is noted that the present embodiment merely provides an embodiment of the present invention and should not be construed as limiting the scope of the present invention.

First, FIG. 1 is a view showing an example of an end-product form of a body adhesive tape according to the present invention; FIG. 2 is a partial front view of the body adhesive tape when viewed from the back side (the side of the adhesive layer); FIG. 3 is a cross-sectional view indicated by the arrow line A-A in FIG. 2; and FIG. 4 is a partially enlarged view showing another embodiment of the recessed grooves.

As shown in FIG. 1, the product P is formed by rolling a long strip-shaped body adhesive tape 1 by a predetermined length (e.g. 5 m, 10 m) with exfoliate paper 2 being held on an adhesive layer 11. In the case of using the body adhesive tape 1 (hereinafter referred to as "tape 1"), the tape 1 is pulled out from the product P by a required length and cut using a cutter or a pair of scissors, and then the exfoliate paper 2 is peeled off to apply the tape to a desired position of a body.

As shown in FIG. 2, in the adhesive layer 11 of the tape 1, a plurality of recessed grooves 111 extending in the tape width direction W and having different lengths are arranged at a spacing in the tape longitudinal direction L. In the present embodiment shown in the figure, recessed grooves 111a, 111b, 111c, and 111d having different lengths increasing stepwise are arranged at regular spacing in the tape longitudinal direction L (refer to FIG. 2).

Specifically, the recessed grooves 111 are arranged in a repetitive pattern array $G_1$ (refer to FIG. 2) in which the length thereof increases and decreases gradually like 111a, 111b, 111c, 111d, 111c, 111b, 111a, 111b, 111c, and 111d . . . .

As for the length of the recessed grooves 111 in the width direction W, the recessed grooves 111a, 111b, 111c, and 111d may be formed to have their respective lengths of, for example, 5 mm, 10 mm, 15 mm, and 20 mm. It is noted that the length of the recessed grooves 111 may be designed freely.

Here, as shown in FIG. 3, the recessed grooves 111 are portions existing in the adhesive layer 11 where the adhesive is formed to have a smaller thickness than the surrounding portions thereof, or may be formed in such a manner, as shown in FIG. 4, that the non-adhesive base material 12 is exposed through the bottom surface portions 1111 thereof. The latter form is advantageous in that the breathability can be further improved through the recessed grooves 111.

FIG. 5 is a plan view of a wide sheet 3a for obtaining the tape 1 to be rolled as the product P when viewed from the side of the adhesive layer. FIG. 6 is a plan view of a sheet 3b according to a variant embodiment in which the recessed grooves 111 are elongated in the tape width direction W when viewed from the side of the adhesive layer.

First, on the sheet indicated by the numeral 3a in FIG. 5, a plurality of pattern arrays G composed of recessed grooves 111a, 111b, 111c, and 111d having different lengths increasing stepwise are formed in the tape width direction W.

When the sheet 3a is cut at, for example, the positions $C_1$ and $C_2$ shown in FIG. 5, it is possible to obtain three long strip-shape pieces of tape 1 including an adhesive layer form as shown in FIG. 2.

On the sheet 3b shown in FIG. 6, a plurality of pattern arrays $G_2$ composed of a total of seven types of recessed grooves 111e, 111f, 111g, 111h, 111i, 111j, and 111k having different lengths increasing stepwise are formed in the tape width direction W, as is the case with the sheet 3a in FIG. 5. When the sheet is cut at the position $C_3$ shown in FIG. 6, it is possible to obtain two long strip-shaped pieces of tape 1.

Sheets in which a group of recessed grooves 111 are formed in a predetermined pattern array in the adhesive layer 11 can be manufactured by, for example, the method shown in FIG. 7. It is noted that although the sheet 3b shown in FIG. 6 is cited as a representative example in FIG. 7, the sheet 3a shown in FIG. 5 and sheets according to exemplary variations shown in FIGS. 8 and 9 below can also be manufactured by the same method.

A pair of roller members Ra and Rb facing each other are installed at predetermined positions. One roller member Ra includes a flat and smooth outer cylindrical surface, while the other roller member Rb is formed with convex portions (not shown in the figure) corresponding to the pattern array of the recessed grooves 111. It is noted that the roller member Ra may be a plate member having a flat and smooth surface.

A sheet 3x in which an adhesive layer 11 is laminated entirely on one surface of a base material 12 is fed from the above or side, etc., into the clearance T between the roller members Ra and Rb before the adhesive becomes solidified. Then, the pattern of the convex portions on the surface of the roller Rb is transferred to the adhesive layer 11 by the pressing forces of the roller members Ra and Rb. It is thus possible to achieve the sheet 3b in which a group of recessed grooves 111 (111e to 111k) arranged in a pattern array $G_2$ is formed in a predetermined number of lines.

It is noted that the embodiment concerning the tape manufacturing method shown in FIG. 7 merely provides an example, and the manufacturing method is not restricted thereto. For example, there is no restriction on forming a group of recessed grooves 111 in the sheet 3x in which the adhesive layer 11 is laminated entirely on one surface of the base material 12 by means of, for example, air blowing, physical scratching or drawing using an acicular member, etc.

The sheet 3c shown in FIG. 8 is characterized, as shown in the Y portion enlarged view surrounded by an ellipse in FIG. 8, in that the group of recessed grooves 111 (111e to 111k) are arranged not at regular spacing in the tape longitudinal direction L but in such a manner that the spacing $d_1$ between 111e and 111f, spacing $d_2$ between 111f and 111g, spacing $d_3$ between 111g and 111h, spacing $d_4$ between 111h and 111i, spacing $d_5$ between 111i and 111j, and spacing $d_6$ between 111j and 111k decrease stepwise, that is, $d_1 > d_2 > d_3 > d_4 > d_5 > d_6$.

Meanwhile, the sheet 3d shown in FIG. 9 is characterized, as shown in the Z portion enlarged view surrounded by an ellipse in FIG. 9, in that the group of recessed grooves 111 (111e to 111k) are arranged not at regular spacing in the tape longitudinal direction L but in such a manner that the spacing $d_1$ between 111e and 111f, spacing $d_2$ between 111f and 111g, spacing $d_3$ between 111g and 111h, spacing $d_4$ between 111h and 111i, spacing $d_5$ between 111i and 111j, and spacing $d_6$ between 111j and 111k increase stepwise, that is, $d_1 < d_2 < d_3 < d_4 < d_5 < d_6$.

As mentioned above, in the embodiments (3c and 3d) shown in FIGS. 8 and 9, the group of recessed grooves 111 (111e to 111k) are not arranged at regular spacing in the tape longitudinal direction L. This causes the array density of the recessed grooves to vary in the tape longitudinal direction L, resulting in providing a functional feature that the degree of stimulus to be provided to fascial and/or muscular tissue under skin by the recessed grooves lifting the skin in a grasping or holding manner varies minutely with the position on the tape.

Making full use of the foregoing features of the pieces of tape 3c and 3d, it is possible to select an array portion of the group of recessed grooves 111 (111e to 111k) in accordance with the intended use for, for example, a body part particularly requiring an increased or reduced degree of stimulus.

For example, in the case of requiring particularly strong stimulus to the knee, elbow, ankle, or heel, etc., it is possible to use the tape 3c or 3d shown in FIG. 8 or 9 in such a manner that the portion around the recessed groove 111 having a higher array density is put on the body part.

On the contrary, in the case of not requiring particularly strong stimulus to a body part to which tape is to be applied, it is only required to use the tape 3c or 3d shown in FIG. 8 or 9 in such a manner that the portion around the recessed groove 111 having a lower array density is put on the body part.

The functions of the thus arranged tape 1 will hereinafter be described with reference to FIGS. 10 and 11.

First, FIG. 10 shows situations where the tape 1 is cut into about a 20 cm length and applied to a body (cubital region), where FIG. 10 (A) shows a situation where the arm is stretched, while FIG. 10 (B) shows a situation where the arm is bent.

The base material 12 constituting the tape 1, which can be expanded and contracted as mentioned above, is expanded and contracted with arm stretching and bending motions (refer to FIG. 10). That is, the tape 1 is applied to the elbow 4a that is kept straight as it is with no expansion (the length of the tape 1a in this case is defined as $l_1$). The length $l_2$ of the expanded tape 1b applied to the elbow 4b that is bent is greater than the length $l_1$ of the tape 1a based on the stretching properties of the base material 12 ($l_2 > l_1$).

FIG. 11 shows cross-sectional views of the tape (in the tape longitudinal direction) illustrating the change in the form of the tape 1 associated with arm stretching and bending motions. FIGS. 11 (A), (B), and (C) show, respectively, states where the elbow is kept straight, the elbow is bent, and the elbow is made straight again. It is noted that although the case where the tape 1 is applied to an elbow will hereinafter be described as a representative example, the position of applying the tape 1 is not restricted to elbows.

As shown in FIG. 11, the length of the tape 1 (particularly in the tape longitudinal direction) changes during the process of the change in the state of the elbow, which results in that the thickness of the adhesive layer 11 changes.

Specifically, the length of the tape changes from $l_1$ to $l_2$ ($l_2 > l_1$) during the transition from the state where the elbow is kept straight (tape 1a in FIG. 11 (A)) to the state where the elbow is bent (tape 1b in FIG. 11 (B)). In this case, in the adhesive layer 11 of the tape 1, the width of the recessed grooves 111 changes from Wa to Wb (Wb>Wa; refer to FIG. 11).

Subsequently, the length of the tape tries to change from $l_2$ to $l_1$ again during the transition from the state where the elbow is bent to the state where the elbow is kept straight again (from the state in FIG. 11 (B) to the state in FIG. 11 (C)). In this case, in the adhesive layer 11 of the tape 1, the width of the recessed grooves 111 changes from Wb to Wa.

The depth of the recessed grooves 111 provided in the adhesive layer 11 also changes with the change of the adhesive layer 11 during the arm stretching and bending motions. Specifically, the depth Da of the recessed grooves 111x of the tape 1a changes to the depth Db of the recessed grooves 111y of the tape 1b (Db<Da) with the reduction in the thickness of the adhesive layer 11 of the tape 1 during the transition from the state where the elbow is kept straight to the state where the elbow is bent.

Then, the thickness of the adhesive layer 11 of the tape 1 is brought back to a level in the state where the elbow is kept straight during the transition from the state where the elbow is bent to the state where the elbow is kept straight again, which results in that the depth Db of the recessed grooves 111y of the tape 1b tries to return to the depth Da of the recessed grooves 111x of the tape 1a.

In the case above, as shown in FIG. 11 (C), each recessed groove 111x of the tape 1a lifts the skin S in a grasping manner (refer particularly to the enlarged view shown in the circle). The skin S once grasped in the recessed groove 111x remains attached to the adhesive portion constituting the inner walls including the bottom surface portion of the recessed groove 111x. Therefore, even if the elbow may be kept straight again, the skin will be kept caught and grasped in the recessed groove 111x.

Alternatively, in the case of employing such an arrangement in which the base material 12 is exposed through the bottom surface portions 1111 of the recessed grooves 111 with no adhesive layer 11 being formed thereon as in the embodiment shown in FIG. 4, the skin S once grasped in the recessed groove 111x through arm stretching and bending motions is less likely to be caught in the recessed groove 111x, when the elbow is kept straight again, to try to return to the state shown in FIG. 11 (A) or an approximation thereof.

As described heretofore, the tape 1 according to the present invention effectively utilizes changes in the width and depth of a group of recessed grooves 111 formed in the adhesive layer 11 associated with motions such as body bending motions to provide tension stimulus to the skin S. In more detail, the tension stimulus is provided not only to the skin S but also to fascial and/or muscular tissue under the skin S.

In the skin, fascial and/or muscular tissue provided with the tension stimulus, stress trying to return to the original position will be generated. Stimulus due to the stress will activate the circulatory system, nervous system, and lymphatic system in the fascial tissue and thereby the muscular tissue that has been deactivated on account of insufficient exercise and/or aging.

Stimulus generated from the thus arranged tape 1 is widely effective in various fields such as bodywork (folk remedies), meridian straightening, reflexology, slimming, functional restoration of fascia and muscles, functional restoration of bones and joints, positional correction of tendons, body massage, body insulation, body protection, relief of stiffness such as shoulder stiffness, pain, and inflammation, etc., taping applications, beautification, and treatment of affected body parts.

INDUSTRIAL APPLICABILITY

The body adhesive tape according to the present invention can be widely utilized in various fields such as bodywork (folk remedies), meridian straightening, reflexology, slimming, functional restoration of fascia and muscles, functional restoration of bones and joints, positional correction of tendons, body massage, body insulation, body protection, relief of stiffness such as shoulder stiffness, pain, and inflammation, etc., taping applications, beautification, and treatment of affected body parts.

BRIEF DESCRIPTION OF THE DRAWINGS

FIG. 1 A view showing an example of an end-product form of a body adhesive tape according to the present invention;

FIG. 2 A partial front view of the body adhesive tape when viewed from the back side (the side of the adhesive layer);

FIG. 3 A cross-sectional view indicated by the arrow line A-A in FIG. 2;

FIG. 4 A partially enlarged view showing another embodiment of the recessed grooves formed in the adhesive layer (11);

FIG. 5 A plan view of a wide sheet (3a) for obtaining the tape (1) to be rolled as the product (P) when viewed from the side of the adhesive layer (11);

FIG. 6 A plan view of a sheet (3b) according to a variant embodiment in which the recessed grooves (111) are elongated in the tape width direction (W) when viewed from the side of the adhesive layer (11);

FIG. 7 A view illustrating a method of manufacturing a sheet in which a group of recessed grooves (111) are formed in a predetermined pattern array in the adhesive layer (11);

FIG. 8 A view showing an exemplary variation of a sheet in which the adhesive layer (11) is formed;

FIG. 9 A view showing another exemplary variation of a sheet in which the adhesive layer (11) is formed;

FIG. 10 Views showing situations where the tape (1) is cut and applied to a body (cubital region); and FIG. 11 Cross-sectional views of the tape (in the tape longitudinal direction) illustrating the change in the form of the tape 1 associated with arm stretching and bending motions.

DESCRIPTION OF THE SYMBOLS

1: Body adhesive tape (Tape)
3a, 3b, 3c, and 3d: Sheets
11: Adhesive layer
12: Base material
111 (111a to 111h): Recessed grooves
1111: Bottom surface portion of recessed groove
112: Convex portion
$G_1$ and $G_2$: Pattern arrays
S: Skin
L: Tape longitudinal direction
W: Tape width direction

The invention claimed is:

1. An adhesive tape comprising:
a stretch base material;
an adhesive layer comprising a plurality of rectilinear grooves disposed on said base material, wherein said grooves extend in a tape width direction and are arranged in an array configuration in a longitudinal direction of said tape;
said grooves not containing adhesive thereby facilitating breathability;
said grooves not extending across the entire width of said tape but having adhesive between said grooves; and
wherein a length of said grooves changes stepwise repeating a gradual increase and decrease in said tape longitudinal direction.

2. The tape of claim 1 wherein a spacing between adjacent grooves decreases stepwise from a shortest groove toward a longest groove.

3. The tape of claim 1 wherein a spacing between adjacent grooves increases stepwise from a shortest groove toward a longest groove.

4. The tape of claim 1 wherein said base material is exposed through said grooves.

5. The tape of claim 1 wherein said grooves are disposed parallel to each other.

6. The tape of claim 1 wherein a width of said grooves changes with expansion and contraction of said tape.

7. The tape of claim 1 wherein a thickness of said adhesive layer changes with expansion and contraction of said tape thereby changing a depth of said grooves.

8. The tape of claim 1 further comprising a peelable exfoliate layer disposed on said adhesive layer.

9. The tape of claim 1 wherein said array comprises a repetitive pattern.

10. The tape of claim 1 wherein said grooves are not arranged at regular spacing in said longitudinal direction.

11. The tape of claim 1 wherein said grooves comprise different lengths.

12. An adhesive tape comprising:
a stretch base material;
an adhesive layer comprising a plurality of rectilinear grooves disposed on said base material, wherein said grooves extend in a tape width direction and are arranged in an array configuration in a longitudinal direction of said tape;
said grooves not containing adhesive thereby facilitating breathability;
said grooves not extending across the entire width of said tape but having adhesive between said grooves; and
wherein a spacing between adjacent grooves decreases stepwise from a shortest groove toward a longest groove.

13. The tape of claim 12 wherein a length of said grooves changes stepwise repeating a gradual increase and decrease in said tape longitudinal direction.

14. The tape of claim 12 wherein said base material is exposed through said grooves.

15. The tape of claim 12 wherein said grooves are disposed parallel to each other.

16. The tape of claim 12 wherein a width of said grooves changes with expansion and contraction of said tape.

17. The tape of claim 12 wherein a thickness of said adhesive layer changes with expansion and contraction of said tape thereby changing a depth of said grooves.

18. The tape of claim 12 further comprising a peelable exfoliate layer disposed on said adhesive layer.

19. The tape of claim 12 wherein said array comprises a repetitive pattern.

20. The tape of claim 12 wherein said grooves are not arranged at regular spacing in said longitudinal direction.

21. The tape of claim 12 wherein said grooves comprise different lengths.

22. An adhesive tape comprising:
a stretch base material;
an adhesive layer comprising a plurality of rectilinear grooves disposed on said base material, wherein said grooves extend in a tape width direction and are arranged in an array configuration in a longitudinal direction of said tape;
said grooves not containing adhesive thereby facilitating breathability;
said grooves not extending across the entire width of said tape but having adhesive between said grooves; and
wherein a spacing between adjacent grooves increases stepwise from a shortest groove toward a longest groove.

23. The tape of claim 22 wherein a length of said grooves changes stepwise repeating a gradual increase and decrease in said tape longitudinal direction.

24. The tape of claim 22 wherein said base material is exposed through said grooves.

25. The tape of claim 22 wherein said grooves are disposed parallel to each other.

26. The tape of claim 22 wherein a width of said grooves changes with expansion and contraction of said tape.

27. The tape of claim 22 wherein a thickness of said adhesive layer changes with expansion and contraction of said tape thereby changing a depth of said grooves.

28. The tape of claim 22 further comprising a peelable exfoliate layer disposed on said adhesive layer.

29. The tape of claim 22 wherein said array comprises a repetitive pattern.

30. The tape of claim 22 wherein said grooves are not arranged at regular spacing in said longitudinal direction.

31. The tape of claim 22 wherein said grooves comprise different lengths.

* * * * *